United States Patent [19]

Geyer et al.

[11] Patent Number: 5,320,848
[45] Date of Patent: Jun. 14, 1994

[54] CHEWABLE DRUG-DELIVERY COMPOSITION

[75] Inventors: Robert P. Geyer, Brookline, Mass.; Vinod V. Tuliani, Media, Pa.

[73] Assignee: Affinity Biotech, Inc., Aston, Pa.

[21] Appl. No.: 889,179

[22] Filed: May 27, 1992

Related U.S. Application Data

[63] Continuation-in-part of Ser. No. 706,343, May 28, 1991, abandoned.

[51] Int. Cl.$^5$ ............................................. A61K 9/28
[52] U.S. Cl. ................................... 424/441; 424/484
[58] Field of Search ............... 424/484, 441; 514/570, 514/629

[56] References Cited

U.S. PATENT DOCUMENTS

| | | | |
|---|---|---|---|
| 2,887,437 | 5/1959 | Klioze et al. | 167/81 |
| 3,108,046 | 10/1963 | Harbit | 167/82 |
| 3,279,988 | 10/1966 | Raff | 167/82 |
| 4,203,997 | 5/1980 | Kuppers et al. | 424/280 |
| 4,206,209 | 6/1980 | Kracauer et al. | 424/234 |
| 4,375,468 | 3/1983 | Dunn | 424/230 |
| 4,517,179 | 5/1985 | Raghunathan | 514/249 |
| 4,695,467 | 9/1987 | Uemura | 424/502 |
| 4,726,966 | 2/1988 | Kawashima et al. | 427/213.36 |
| 4,755,387 | 7/1988 | Tzeghai et al. | 424/450 |
| 4,761,407 | 8/1988 | Campan et al. | 514/179 |
| 4,831,058 | 5/1989 | Pankhania et al. | 514/570 |
| 4,835,186 | 5/1989 | Reuter et al. | 514/570 |
| 4,835,187 | 5/1989 | Reuter | 514/570 |
| 4,835,188 | 5/1989 | Ho | 514/570 |
| 4,837,255 | 6/1989 | Dechow | 524/23 |
| 4,859,472 | 8/1989 | Demmer et al. | 424/489 |
| 4,865,851 | 9/1989 | James et al. | 424/498 |
| 4,880,830 | 11/1989 | Rhodes | 424/470 |
| 4,882,152 | 11/1989 | Yang et al. | 424/440 |
| 4,882,167 | 11/1989 | Jang | 424/468 |
| 4,894,233 | 1/1990 | Sharma et al. | 424/440 |
| 4,916,161 | 4/1990 | Patell | 514/570 |

FOREIGN PATENT DOCUMENTS 2081092A 7/1981 United Kingdom.

OTHER PUBLICATIONS

Brochure entitled "Ac-Di-Sol" Croscarmellose Sodium, NF (Accelerates DisSolution), FMC Corporation 1988.

*Primary Examiner*—Thurman K. Page
*Assistant Examiner*—Benston, Jr. William E.
*Attorney, Agent, or Firm*—Woodcock Washburn Kurtz Mackiewicz & Norris

[57] ABSTRACT

A non-aqueous, chewable composition for oral delivery of unpalatable drugs is provided. The composition contains the drug intimately dispersed or dissolved in a pharmaceutically-acceptable lipid that is solid at room temperatures. The composition also has a matrix that contains a granulating agent for the total composition and a rapid dispersal agent and optionally additives such as buffering agents, flavoring agents, surfactants, and the like. Methods for the preparation of the chewable compositions are also provided.

26 Claims, No Drawings

CHEWABLE DRUG-DELIVERY COMPOSITION

This application is a continuation-in-part of application Ser. No. 706,343, filed on May 28, 1991, and now abandoned.

FIELD OF THE INVENTION

This invention relates to a non-aqueous, chewable composition for oral delivery of pharmaceutically-active compounds. More particularly, it relates to lipid-based, chewable formulations for the oral delivery of unpalatable drugs, and processes for preparing the same. The compositions are designed to be chewed and masticated and then swallowed while not only masking the taste of the drug but also providing a pleasant mouth taste and feel.

BACKGROUND OF THE INVENTION

Formulations for oral delivery of various pharmaceutically-active compounds, particularly unpalatable ones such as aspirin, ibuprofen, cimetidine, acetaminophen, erythromycin, or the like, are well known in the art. Generally, unacceptable taste characteristics due to acidity, bitterness, burning in the back of the throat, or odorousness, have been overcome, by coatings, capsules, flavoring agents or combinations of these features. See for example, formulations which are intended to be swallowed whole, such as those disclosed in U.S. Pat. No. 4,726,966, which coats granular ibuprofen with an acrylic acid resin in the presence of an organic solvent and water; U.S. Pat. No. 4,835,186, which discloses spray-drying ibuprofen in a suspension of colloidal silica, alcohol, and cellulose acetate; and U.S. Pat. No. 4,916,161, which discloses coating ibuprofen via a wet granulation method using certain methyl cellulose phthalates as taste-masking agents. Each of these formulations, however, has been devised in order to momentarily disguise or prevent these objectionable features while the compound is passing through the mouth and throat and being swallowed without being masticated.

U.S. Pat. No. 4,755,387 employs lipids to coat therapeutic agents such as aspirin in order to assure slow absorption in the stomach. Alternative timed-release aspirin formulations are disclosed in U.S. Pat. No. 4,375,468, employing such slow-release coating agents as waxes, fats, cellulose esters, etc., alone or in various combinations. This patent claims a slow-release formulation comprising aspirin, hydrogenated vegetable oils, and saccharides prepared in an organic solvent solution. Similarly, U.S. Pat. No. 4,761,407 discloses a formulation for oral administration of various active agents which are first dissolved in a heated liquid organic phase, followed by mixing this liquid with a second, different organic phase, and cooling this liquid to a solid dosage form.

Unfortunately, for certain classes of ill persons, or even in veterinary applications, swallowing of a tablet or capsule containing these unpalatable compounds is difficult or impossible; this is particularly so in the very elderly or in young children. This situation leads to problems with noncompliance in maintaining the dosage schedules for the patients. Moreover, many such formulations, as evidenced by the cited art, are very complex in their composition or preparation or both, and thus costly and difficult to make. See, for example, the chewable formulation disclosed In U.S. Pat. No. 4,882,152 comprising an active ingredient pre-coated with glycerides, lecithin, polyoxyalkylenes, or polyalkylene glycols, and mixed into a binder comprising a gelatin, a sweetener, glycerin, and water.

A relatively simple formulation, especially of such unpalatable drugs as aspirin, ibuprofen, cimetidine, acetaminophen, erythromycin, or the like which could readily be chewed before swallowing without suffering the bitterness, burning, or unpleasant taste or odor of these unpalatable compounds would be highly desirable.

SUMMARY OF THE INVENTION

In accordance with the present invention, there is now provided in one aspect, a non-aqueous, chewable composition which disintegrates rapidly in the mouth for the delivery of unpalatable pharmaceutically-active compounds comprising a therapeutically-effective amount of one or more unpalatable pharmaceuticals intimately dispersed or dissolved in a pharmaceutically-acceptable lipid in which each component is solid at ambient temperatures, and a matrix for said drug and lipid comprising (a) one or more solid granulating agents, and, optionally, (b) minor amounts of additives such as buffering agents, sweeteners, flavoring agents, rapid dispersal agents, or the like, or mixtures thereof. "Chewable" products, as used herein, can be in the form of compressed tableted material, or in the form of an uncompressed powder. The chewable composition preferably contains a rapid dispersal agent that is a cellulose derivative, more preferably the dispersal agent is croscarmellose sodium. The chewable composition is formulated to disperse and disintegrate rapidly in the mouth while masking the taste of the drug throughout the mastication process.

It is important that the components and final product be essentially non-aqueous, since moisture can adversely affect the taste of the composition if present before being chewed. Small amounts of oils, surfactants, or like non-aqueous liquids may also be added, however, If necessary, to control the consistency of the product.

By the term "unpalatable" is meant any bad taste caused by acidity, bitterness, burning in the back of the throat, or malodorousness. A particular problem in that regard is the burning in the back of the throat caused by the well-known analgesic ibuprofen, and related compounds.

Commonly known, pharmaceutically acceptable additives for orally-administered drugs such as sweeteners, flavoring agents, dispersants, buffering agents, and the like may be included in amounts that do not adversely affect the novel properties of the formulation claimed herein. Again, however, since it is necessary that the final composition be essentially non-aqueous, no water or water-based materials should be used; and when necessary, low humidity conditions should be used, e.g., with aspirin, certain antibiotics, and the like.

Moreover, it is important in carrying out the manufacture of the products of this invention that no solvents be employed in order to avoid imparting toxic materials to the chewable product and/or any adverse change to the physical properties of the ingredients.

These novel compositions are particularly advantageous, as compared with prior chewable formulations, in that they effectively prevent, for example, the back-of-the-throat burning sensation caused by ibuprofen when chewed, yet they contain few components, and thus are easy and economical to prepare.

DETAILED DESCRIPTION OF THE INVENTION

In one embodiment of this invention, the novel compositions may readily be prepared by first heating together, under mildly elevated temperatures of from about 55° to 95° C., the active pharmaceutical ingredient (hereinafter called "drug"), and the lipid, wherein at least the lipid and desirably both components are melted, to form a first melted phase whereby the drug is dispersed or dissolved in the melted lipid. The mixture is then cooled, preferably rapidly by chilling, to about room temperature or below, to provide a solid in which the drug is dispersed or dissolved in a continuous lipid phase. In this way, the drug is in intimate contact with the lipid. It will further be understood that in the case of heat-sensitive drugs, the drug may be added to the lipid after it has cooled down to a point just short of solidification at room temperature. Finally, we have found that the drug and lipid can be mixed vigorously at room temperature, to disperse the drug in the lipid in fine particulate form, i.e. without first melting the lipid and drug. This mixing of the drug and lipid without first melting them can generally be achieved by use of mechanical mixers for 5-10 minutes at temperatures of from about 10°-40° C.

The drug-lipid mixture is then reduced to a powder and blended with a finely ground granulating agent for the drug and lipid to form a dry powder. Alternatively, the ground granulating agent can be dispersed in melted lipid phase before cooling, and the resulting cooled mixture then reduced to a powder. This may be done either before or after the drug is added. By the term "granulating agent" is meant any material which facilitates formation of a particulate, i.e. granular, product. When ground, the powder may, if desired, then be tableted, coated, encapsulated or the like by methods known in the pharmaceutical art for use as a chewable composition for oral delivery of the drug.

In summary, and for purposes of the "hot melt" method, the drugs most advantageously employed, in addition to being unpalatable, are those such as ibuprofen which are solid at room temperature but which desirably have good thermal stability and low melting points, i.e. they may be readily liquified by heat in the course of formulating them without affecting their activity, generally at temperatures no greater than about 95° C. Drugs which do not melt easily may also be employed in this invention by dispersing them in the melted lipid in finely ground particulate form. By "finely ground" is generally meant particles which pass through sieves of about No. 80 to 120 Tyler standard, although these sizes may be varied somewhat according to the drug. Typical of these drugs are such compounds as aspirin, acetaminophen, cimetidine, ranitidine, erythromycin, piroxicam, esters and salts thereof, and the like. As a third alternative, the drug and lipid are both mixed at room temperature in a non-hot melt procedure.

In another embodiment of the invention, a spray congealing process is employed to produce the chewable composition. The spray congealing process is advantageous in that a uniform and fine dispersion of the drug in the lipid phase is formed. The spray congealing process also provides particles that are uniform and spherical in shape. The particles thus produced provide for a pleasing mouthfeel and texture upon chewing and swallowing.

The spray congealing procedure is performed by first admixing the drug and lipid in a molten state, above the melting point of either component, to form a uniform mixture. This mixture is then fed into a spray congealing apparatus which sprays the mixture through either a stationary nozzle or through a rotary atomizer. The spray congealing apparatus generally operates to solidify the atomized liquid mixture, i.e. droplets, and to allow the solidification to proceed by way of the droplets coming into contact with a cooler gaseous environment, usually air. The particle size can be altered, and generally particle sizes of from about 10-150 microns, preferably about 40-140 microns are acceptable. These particles form a powder when accumulated and are found to have almost no taste of the drug when chewed.

The spray congealing process can be varied in many ways to produce compositions falling within the ambit of the invention. Preferably, the mass ratio of the drug to lipid in the process can vary from about 1:2 to 2:1. The drug may be either in molten or particulate form during the process. After the drug and lipid mixture is atomized and solidified by the spray congealing process, the granulating agent and any of the various additives can be blended with the particles. This blend then can be optionally pressed into tablet form.

The lipids employed herein include glycerol fatty-acid esters, preferably triglycerides, having from about 12 to 30 carbon atoms in each chain, such as tristearin, tripalmitin, or ethyl palmitate, as well as coconut oil; lipid-containing low-melting materials such as chocolate; waxes, resins, high molecular weight glycols, e.g. polyoxyethylene glycols (20-400 repeating units), as well as hydrogenated fats and oils of 12-30 carbon atom chains, or mixtures thereof. Of these, glycerol esters are preferred. As stated above, these lipids are normally solid at room temperature, but desirably readily melt with the application of mild temperatures, i.e., about 55 to 95° C. Included are both pure compounds and mixtures whose components may individually fall outside this range, but whose average melting point is within this range.

In order to ensure a final product of proper chewable consistency, it is necessary that the composition also include a matrix for the drug and lipid comprising principally (a) granulating agents which serve both to aid in forming a tableted product, and, desirably, to disperse the composition when chewed, and (b) any optional additives. As used herein, the matrix is the balance of the composition besides the drug and lipid. Thus, the term "matrix", as used hereinafter, includes not only the granulating agent but optionally, minor amounts of additives such as flavoring agents, coloring agents, sweeteners, dispersing agents, buffering agents, or the like, as described below. The granulating agents, which should be in solid form at room temperature, include such compounds as sorbitol, mannitol, dextrose, sucrose, lactose, or like sugars, starches, or mixtures thereof. While these agents can be substantially tasteless, e.g. starches, those having a sweet taste are preferred.

Incorporation of the matrix in with the drug/lipid phase may be achieved by simply blending the two components, with agitation, until a uniform mixture is formed. However, it has been found that by premixing a small amount of the neat lipid with the matrix prior to blending with the drug and remaining lipid, an improvement in the taste of the final product is obtained.

One preferred additive is a buffering agent for the drug, such as sodium bicarbonate, sodium phosphates, or the corresponding calcium salts or the like. Use of such an agent will depend principally on the nature, concentration, and taste of the drug involved; the need for this agent can readily be determined by taste tests. Such agents, it has been found, are particularly effective in eliminating the burning in the throat caused by ibuprofen. The buffering agent can be present in the drug composition in an amount of from about 0.1 to about 10 weight percent, preferably from about 1 to about 5 weight percent.

Other optional additives which may be included in the final product are, as stated above, coloring agents; sweeteners, including additional amounts of granulating agents, such as sorbitol or dextrose, or synthetic sweeteners such as aspartame (Nutrasweet®, Nutrasweet Co., Deerfield, Ill.); and flavoring agents such as additional chocolate and other flavoring agents that are well known to those in the drug delivery art, preferably the flavoring agent does not also act as a lipid as defined herein. The flavoring agent can be present in the drug compositions in an amount of from about 0.2 to about 6 weight percent, preferably from about 0.5 to about 5 weight percent.

Rapid dispersal agents such as starches, cellulose, or derivatives thereof; or the like; or mixtures thereof can also be used as additives. The amount of the rapid dispersal agent present in the composition can range from about 1 to about 30 percent, preferably from about 2 to about 20 percent, more preferably from about 7 to about 15 weight percent. In addition, the rapid dispersal agent or agents used in the compositions preferably contain at least one preferred rapid dispersal agent, examples of such preferred rapid dispersal agents include sodium starch glycolate, available as Explotab, manufactured by Edward Mendell Co., pregelatinized corn starch, available as Starch 1500, manufactured by Colorcon, Inc., crospovidone, available as Polyplasdone XL series, manufactured by International Specialty Products, and croscarmellose sodium and derivatives thereof, available as Ac-Di-Sol manufactured by FMC Corp, croscarmellose sodium being particularly preferred. The amount of the preferred rapid dispersal agent ranges from about 0.1 to about 5 percent, preferably from about 0.25 to about 2.5 weight percent of the composition. Unless such agents are lipid-soluble, it is preferable to first add them in with the granulating agent before its final mixing with the lipid phase. It is noted that certain additives can be used as both a lipid or granulating agent and also as an additive.

Additionally, the consistency of the matrix, and thus the final product, can be adjusted when necessary to avoid undue hardness or poor mouth feel, by the incorporation of minor amounts of other additives such as oils or surfactants into the matrix. Thus, for example, there may be employed phospholipids such as soybean-derived lecithin, oils such as soy oil, corn oil, cocoa butter, cottonseed oil, or like softening additives. For purposes of assuring rapid dispersal in the mouth, there may also be used in the matrix the above mentioned rapid dispersal agent such as methyl cellulose and derivatives thereof, starch, and preferably croscarmellose sodium or the like which aid in dispersing the chewed material rapidly when moistened in the mouth.

Consistency can also be varied at any point in the process by controlling the degree of grinding of the cooled, hardened product, i.e. the particle size, as well as by conventional tableting or compacting methods used to vary tablet hardness.

The amounts of each of the components in the final product may be varied considerably, depending upon the nature of the drug, the unit dosage desired, and the need for any given additives. Generally, however, the drug may range in weight from about 0.1% to 75%, more preferably 0.5% to 40%, and the lipid 5% to 50%, more preferably 10% to 40%, based on the total weight of the composition, with the matrix, including any optional additives, comprising the balance. Thus, the matrix may comprise from about 10 to 94% of the weight of the total composition with the optional additives, if any, comprising up to about 50% wt., preferably up to about 20% of the weight of the matrix, most preferably from about 10-20% wt. of the matrix, however in some cases from about 10-30% wt. of the matrix. These optional additives, when used in combination, may first be made up in the form of a mix for addition to the granulating agent in the form of a premix.

In a further, more preferred embodiment, it has been found that when the addition of the matrix, and any other additives, to the initial drug/lipid phase is carried out stepwise, i.e. incrementally, with thorough mixing at each step until the desired final drug concentration is reached, this final product, surprisingly, has an even better taste as contrasted with the formulations obtained by adding the entire quantity of matrix at one time. This incremental addition of matrix may be applied to the drug/lipid phase of either the "hot-melt" or room temperature-formed mixtures.

In yet another method for preparing the compositions of this invention, it has been found that in certain instances, as for example when the drug cimetidine, acetaminophen, or aspirin, together with the lipid or lipid-containing material such as chocolate, has been powdered, it may be sandwiched between layers of matrix which may also contain additional amounts of said lipid in order to further reduce the unpalatable taste of the drug.

Ibuprofen formulations are particularly preferred in the chewable format of the present invention. Such ibuprofen compositions contain 0.1-75% wt., preferably 0.5-40% wt., most preferably about 1-25% wt. ibuprofen. The lipid content is from 5-50% wt., preferably 10-40% wt., most preferably 15-30% wt. and preferably the lipid is a glycerol ester, especially a triglyceride. The granulating agent content is from 25-75% wt., preferably 30-70% wt., most preferably 40-60% wt. The granulating agent is preferably mannitol. The ibuprofen composition may also contain dispersal agents in an amount of from 1-30% wt., preferably from 2-20% wt., most preferably from 7-15% wt. These dispersal agents preferably include hydroxyethyl cellulose, corn starch, croscarmellose sodium (Ac-Di-Sol made by FMC Corp.), and mixtures thereof. Preferably, the dispersal agents include a mixture such as 4-7% wt. hydroxyethyl cellulose, 2-5% wt. corn starch, and 1.5-4.5% wt. croscarmellose sodium. The ibuprofen composition may also contain flavoring agents in an amount of from about 0.2-6% wt, preferably about 0.5-5% wt. Flavoring agents such as acids including citric acid, ascorbic acid, DL-malic acid, or mixtures thereof from about 0.2-2% wt., preferably 0.5-1.5% wt can be included along with other flavoring agents such as grape or citrus flavor can be added from 0.1-4% wt., preferably from 0.5-3% wt. Sweeteners, particularly aspartame, can also be added from about 0.5-10% wt., preferably 2-8% wt., most preferably 3-6% wt. A lubricant can be admixed to the composition to aid in the processing of tablets, the preferred lubricant is magnesium stearate and is present in an amount of from 0.5-7% wt., preferably 1.5-4.5% wt. Other additives such as antioxidants and chelating agents can also be added to the composition.

The invention will now be illustrated by, but is not intended to be limited to, the following examples. In these examples it will be understood that for purposes of calculating weight percent of ingredients, regardless of when they are added, all components other than the drug and lipid are calculated as part of the weight of the matrix.

EXAMPLE 1

Four hundred mg lipid (tripalmitin, 90+%, Sigma Chemicals, St. Louis, Mo.) was melted in a vial, using a water bath maintained at around 85.C. To the melted tripalmitin, 400 mg ibuprofen powder was added. Once the drug melted, it was stirred with the melted lipid to produce a homogeneous mixture. Forty mg of sorbitol granulating agent was added to this mixture and mixed into it to produce an even dispersion. The vial was then quickly immersed in an ice bath, while stirring was carried out continuously. In a very short period of time, the mixture was seen to become solid. The material was then powdered. One hundred mg sorbitol powder and 40 mg aspartame powder were added to the final powder mix and stirred into it. The resulting formulation contained ibuprofen at a concentration of about 40% (w/w). The burning sensation associated with the taste of ibuprofen was effectively masked in this preparation. The only taste that could be detected was the sweet taste of the sorbitol and aspartame. This granulated ibuprofen preparation was chewable and contained an adult dose of the drug with no unpleasant taste or sensation.

EXAMPLE 2

Another formulation was prepared in which the internal phase or drug was cimetidine. In this case, 200 mg of cimetidine was stirred into 600 mg tripalmitin at 85° C. The lipid was in a liquid state while the drug was present as a dispersed solid, since the temperature was below its melting point. The drug was stirred into the lipid and 60 mg sorbitol was added. After the cooling and powdering steps, 100 mg of additional sorbitol together with 40 mg aspartame was also added to the mixture. The resulting powdered preparation had a marked decrease in bitter taste compared to the neat drug, and it also had a pleasant, sweet taste.

EXAMPLE 3

In the following formulation, a higher concentration of ibuprofen than normally employed in the final product was incorporated into a preparation of this invention; however, a slight burning sensation was detected. In order to counteract it, some sodium bicarbonate powder was used in the preparation, as buffering agent.

Thus, 700 mg melted ibuprofen was added to 100 mg molten tripalmitin at 85 C. After the ibuprofen was melted and mixed with the tripalmitin, 60 mg of sorbitol was added and the entire mixture cooled while continually stirring. After powdering, 40 mg aspartame, 50 mg sorbitol and 50 mg sodium bicarbonate were added to the mixture. The final powdered preparation had a sweet taste and a substantial reduction of the burning sensation which occurred when no sodium bicarbonate was present.

EXAMPLE 4

In the following formulation, the drug/lipid phase was mixed at room temperature without final melting either component. Aspirin, 320 mg, was placed in a vial and 106 mg of hydrogenated vegetable oil (Sterotex NF, Karlshamns Lipid Specialties USA, Columbus, OH) was added to it. This was mixed at room temperature to produce a well-blended mixture. A premix containing 11.5 parts mannitol, 5 parts 100-mesh sorbitol, 1 part corn starch and 2.5 parts Nutrasweet was then prepared separately. Five hundred seventy mg of this premix was added in increments to the lipid/aspirin mixture in increasing amounts. After each addition of premix, the mixture was well blended using hand stirring. The resulting mixture was then compressed into a pill at 2500 psi pressure. The resulting tablet was pleasant and slightly tart tasting.

EXAMPLE 5

Two hundred mg ibuprofen was co-melted with 200 mg hydrogenated vegetable oil, (Sterotex NF) at 85.C. It was well mixed then cooled to solidify the mixture. The resulting solid was ground to a fine powder. To this lipid/drug mixture was added 1 gram of premix containing 11.5 parts mannitol, 5 parts 100 mesh sorbitol, 1 part corn starch and 2.5 parts Nutrasweet. This was added in stepwise increments with stirring after each addition. One $\mu$l oil of wintergreen was then added to the mix. The resulting mixture is then compressed into a pill at 10,000 psi pressure. The tablet was pleasant and sweet tasting.

EXAMPLE 6

Seventy-five mg of ranitidine was mixed with 75 mg hydrogenated vegetable oil (Sterotex K) and the lipid melted at about 90.C. The mixture was cooled to room temperature, solidified, and powdered. To this was added 850 mg finely powdered premix containing 11.5 parts mannitol, 5 parts 100 mesh sorbitol, 1 part cornstarch, 2.5 parts Nutrasweet and 2.2 parts Sterotex K lipid. The premix was added, stepwise, with mixing. Twenty-five mg ground citric acid, 8 $\mu$l oil of sweet orange, and 25 mg powdered sodium chloride were also added to complete the formulation, which was compressed at 2500 psi to give a pleasantly tart-tasting tablet.

EXAMPLE 7

In the following formulation, the lipid, including chocolate, was first mixed with the matrix prior to addition of the drug.

The chocolate mix was prepared by melting 6.5 g Baker's unsweetened chocolate (Kraft General Foods, Inc., White Plains, N.Y.) and 1.5 g Sterotex K at 85° C. To this well mixed melted mixture was added 7.0 g premix containing 11.5 parts mannitol, 5 parts 100 mesh sorbitol, 1 part cornstarch and 2.5 parts Nutrasweet. The entire mixture was then well mixed while hot, and then cooled to a solid mix. Grinding the solid mix gave a chocolate matrix powder. Two hundred mg cimetidine was then placed in a vial and 800 mg chocolate matrix powder was added. This was heated to soften the matrix as the cimetidine was stirred into it. An additional 103 mg aspartame was also mixed into the softened blend. The resulting mixture was cooled, solidified, ground to a powder and compressed at 2500 psi to give a tablet that had a pleasant taste of bittersweet chocolate.

EXAMPLE 8

One hundred mg erythromycin ethyl succinate was added to 100 mg Sterotex N F that had been melted in a vial and allowed to cool somewhat without solidification. After the drug was added, the mixture was well mixed to produce a solid blend. The mix was then ground to a fine powder. Eight hundred mg premix containing 11.5 parts mannitol, 5 parts 100 mesh sorbitol, 1 part cornstarch and 2.5 parts Nutrasweet was then added in small sequential aliquots and stirred after each addition. The resulting mixture was then compressed at 2500 psi to give a sweet tasting tablet with no bitter taste.

EXAMPLE 9

In order to demonstrate that ibuprofen formulated in the lipid matrix is still available for absorption in the gut, the following study was performed in rats. In a process similar to that used in Example 5, a tablet containing 100 mg ibuprofen was prepared by the hot technique in which the drug and lipid were both co-melted. The final tablet formulation contained 100 mg ibuprofen, 100 mg lipid (Sterotex HM, Karlshamns Lipid Specialties USA, Columbus, OH), and 800 mg matrix which comprised 11.5 parts mannitol, 5 parts 100 mesh sorbitol, 1 part corn starch and 2.5 parts Nutrasweet. A pressure of 5000 psi was used in the tableting process.

The tablets were crushed in water to give a suspension containing 20 mg ibuprofen/ml of suspension. Rats were then gavage with the suspension such that each rat received 0.5 ml suspension, corresponding to 10 mg ibuprofen. A total number of 30 rats was used. Separate groups of 5 rats each were gavage and then bled after gavage at 0.25 hr., 0.5 hr., 1 hr., 2 hrs., 4 hrs., and 6 hrs. Blood was obtained from these rats by caridac puncture and the serum was separated. The serum was analyzed for ibuprofen concentration by Roche Biomedical Laboratories (Burlington, NC). Results from these analyses are shown in Table 1.

TABLE 1

| Time After Gavage (hr.) | Mean Serum Ibuprofen Concentration (mcg/ml) | Standard Error for Mean Serum Ibuprofen Concentration (mcg/ml) |
| --- | --- | --- |
| 0 | 0 | 0 |
| 0.25 | 4.2 | 2.02 |
| 0.50 | 22.6 | 8.28 |
| 1.0 | 50.4 | 12.04 |
| 2.0 | 15.2 | 4.68 |
| 4.0 | 11.2 | 2.94 |
| 6.0 | 3.3 | 1.41 |

The data demonstrate that the ibuprofen was available in the bloodstream of the rats. The area under the concentration vs. time curve was 95.92 mcg.hr./ml which is not significantly different than the area obtained with an uncoated ibuprofen. This means that the lipid used in our invention does not significantly adversely affect the serum absorption of the drug.

EXAMPLE 10

A molten mixture of Sterotex HM (Karlshamns Lipid Specialties USA, Columbus, Ohio 43201) and ibuprofen (Ethyl Corporation, Baton Rouge, La. 70801) in a 2:1 ratio was spray congealed. The product was a powder consisting of spherical particles with a median size of 118 microns.

In a high speed grinder, 10 g hydroxyethyl cellulose (Spectrum Chemical Manufacturing Corporation, Gardena, Calif.), 2 g citric acid (Spectrum Chemical), 4 g Nutrasweet, 10 g mannitol (Spectrum Chemical) were mixed with 2 ml grape flavor. The mixture was ground at high speed in 2 periods of 15 seconds each. After grinding, the material was well mixed with a spatula. Once the ground mix was prepared, 14 g were taken and transferred to a PK Twin Shell Dry Blender (Patterson-Kelley Co., East Stroudsberg, Pa).

The spray congealed powder containing Sterotex HM and ibuprofen in a 2:1 ratio was sifted through a 60 mesh Tyler equivalent screen. Of the powder that passed through the screen, 30 g were taken and added to the material present in the PK Twin Shell Dry Blender. Also added to the material in the Blender were 2 g magnesium stearate (Witco Corporation, NY, N.Y.), 2 g Ac-Di-Sol (FMC Corporation, Philadelphia, Pa.), 48.5 g mannitol powder (Spectrum Chemical), 2 g Nutrasweet, and 3.38 g corn starch (Spectrum Chemical). The blender was then switched on and the contents allowed to mix for 10 minutes.

The well-mixed powder was then transferred to the feed hopper of a Korsch EK-0 Tablet Press (Korsch Tableting Inc., Somerville, N.J.). Tablets weighing about 500 mg each and containing about 50 mg ibuprofen were produced by the press using the composition and process described above.

The chewable tablets produced were found to have a sweet taste and a pleasant grape flavor when they were tasted, chewed and swallowed. No bitterness or burning at the back of the throat or on the tongue normally attributed to ibuprofen was observed.

What is claimed is:

1. A non-aqueous, chewable composition which disintegrates rapidly in the mouth for oral delivery of unpalatable drugs in which the unpalatable taste of the drug is masked during mastication, comprising:
    (a) a therapeutically-effective amount of one or more unpalatable drugs intimately dispersed in a solid pharmaceutically-acceptable lipid coating, which lipid is solid at ambient temperature, or mixtures of said lipids, wherein the lipid is present in the composition in an amount of from 5-50 percent by weight.
    (b) a matrix for said drug and lipid, said matrix consisting essentially of:
        (i) one or more granulating agents,
        (ii) a rapid dispersal agent in an amount of from about 2 to about 20 weight percent of the composition, wherein the rapid dispersal agent is blended with the solidified lipid coated drug, and
        (iii) optionally minor amounts of additives selected from the group consisting of flavoring agents, coloring agents, buffering agents, sweeteners, oils, and surfactants.

2. The composition of claim 1 wherein the rapid dispersal agent comprises at least one agent selected from the group consisting of croscarmellose sodium, sodium starch glycolate, pregelatinized corn starch, and crospovidone.

3. The composition of claim 2 wherein the composition is a compressed tablet.

4. The composition of claim 3 wherein the granulating agent is blended with the solidified lipid coated drug.

5. The composition of claim 3 wherein the rapid dispersal agent comprises croscarmellose sodium.

6. The composition of claim 5 wherein the croscarmellose sodium is present in an amount from about 0.1 to about 5 percent by weight of the composition.

7. The composition of claim 5 wherein the drug is ibuprofen, acetaminophen, aspirin, cimetidine, piroxicam, ranitidine, or erythomycin.

8. The composition of claim 7 wherein the croscarmellose sodium is present in an amount from about 0.1 to about 5 percent by weight of the composition, and the composition further comprises a non-lipid flavoring agent.

9. The composition of claim 8 wherein the granulating agent is selected from the group consisting of mannitol, sorbitol, dextrose, sucrose, and lactose.

10. The composition of claim 9 wherein the drug is ibuprofen and is present in an amount of from about 0.5 to about 40 weight percent; the granulating agent is present in an amount of from about 30-70 weight percent; and the non-lipid flavoring agent is present in an amount of from about 0.2 to about 6 weight percent.

11. A non-aqueous, chewable composition which disintegrates rapidly in the mouth for oral delivery of ibuprofen, consisting essentially of:
(a) a therapeutically-effective amount of ibuprofen intimately dispersed in a solid pharmaceutically-acceptable lipid or mixture of lipids; and
(b) a matrix for the ibuprofen and the lipid, the matrix consisting essentially of at least one granulating agent and at least one rapid dispersal agent, and optionally minor amounts of additives selected from the group consisting of flavoring agents, coloring agents, buffering agents, sweeteners, oils, and surfactants, wherein the rapid dispersal agent is blended with the solidified lipid coated drug.

12. The chewable ibuprofen composition of claim 11 wherein the ibuprofen is present in an amount of from 0.5-40 percent by weight.

13. The chewable ibuprofen composition of claim 12 wherein the lipid is present in an amount of from 5-50 percent by weight.

14. The chewable ibuprofen composition of claim 13 wherein the rapid dispersal agent is present in an amount of from 7-15 percent by weight.

15. The chewable ibuprofen composition of claim 14 further containing from about 1 to about 5 weight percent buffering agent.

16. The chewable ibuprofen composition of claim 14 further containing 30-70 percent by weight granulating agent, from about 0.5-5 percent by weight flavoring agents, and from about 2-8 percent by weight sweetener.

17. The chewable ibuprofen composition of claim 14 wherein the composition is a compressed tablet.

18. The chewable ibuprofen composition of claim 17 wherein the granulating agent is blended with the solidified lipid coated ibuprofen.

19. The chewable ibuprofen composition of claim 17 that has been pressed at a pressure of from 5000 to 10,000 psi.

20. A non-aqueous, chewable composition which disintegrates rapidly in the mount for oral delivery of unpalatable drugs in which the unpalatable taste of the drug is masked during mastication, comprising:
(a) solidified drug particles consisting essentially of a therapeutically-effective amount of one or more unpalatable drugs intimately dispersed in a solid pharmaceutically-acceptable lipid coating, which is solid at ambient temperature, or mixtures of said lipids, wherein the lipid is present in the composition in an amount of from 5-50 percent by weight; and
(b) matrix for said solidified drug particles, said matrix comprising:
(i) one or more granulating agents, and
(ii) a rapid dispersal agent in an amount of from about 2 to about 20 weight percent of the composition.

21. The composition of claim 20 further comprising, in the matrix, minor amounts of at least one additive selected from the group consisting of flavoring agents, coloring agents, buffering agents, sweeteners, oils, and surfactants.

22. The composition of claim 21 wherein the drug comprises ibuprofen, acetaminophen, aspirin, cimetidine, piroxicam, ranitidine, or erythomycin.

23. The composition of claim 22 wherein the composition is in the form of a compressed tablet.

24. The composition of claim 21 wherein the drug comprises ibuprofen.

25. The composition of claim 24 wherein the rapid dispersal agent is present in an amount of from 7-15 percent by weight.

26. The composition of claim 24 wherein the ibuprofen is dissolved in the lipid.

* * * * *

UNITED STATES PATENT AND TRADEMARK OFFICE
CERTIFICATE OF CORRECTION

PATENT NO. : 5,320,848
DATED : June 14, 1994
INVENTOR(S) : Robert P. Geyer, Vinod V. Tuliani It is certified that error appears in the above-indentified patent and that said Letters Patent is hereby corrected as shown below:

Column 12, line 24, insert --lipid-- after "which"

Signed and Sealed this

Twenty-third Day of May, 1995

Attest:

BRUCE LEHMAN

Attesting Officer     Commissioner of Patents and Trademarks